United States Patent
Wood et al.

(10) Patent No.: US 6,187,532 B1
(45) Date of Patent: Feb. 13, 2001

(54) DOUBLE-STRANDED CONFORMATIONAL POLYMORPHISM ANALYSIS

(75) Inventors: Michael Wood, Palo Alto; Reuel Van Atta, Mountain View; David Albagli, Palo Alto, all of CA (US)

(73) Assignee: Naxcor, Menlo Park, CA (US)

( * ) Notice: Under 35 U.S.C. 154(b), the term of this patent shall be extended for 0 days.

(21) Appl. No.: 08/742,376

(22) Filed: Nov. 1, 1996

Related U.S. Application Data

(60) Provisional application No. 60/007,239, filed on Nov. 3, 1995.

(51) Int. Cl.[7] ............................. C12Q 1/68; C12P 19/34; C07H 21/04
(52) U.S. Cl. ............................ 435/6; 435/91.2; 435/810; 536/24.3
(58) Field of Search ............................. 435/6, 91.2, 810; 536/24.3; 935/8, 10, 78

(56) References Cited

U.S. PATENT DOCUMENTS

| | | | |
|---|---|---|---|
| 5,082,934 | * 1/1992 | Saba | 536/17.6 |
| 5,616,464 | 4/1997 | Albagli et al. | 435/6 |
| 5,652,096 | * 7/1997 | Cimins | 435/6 |

FOREIGN PATENT DOCUMENTS

0329311 * 8/1989 (EP).

OTHER PUBLICATIONS

Kotze et al., "Nonradioactive Multiplex PCR Screening Strategy for the Simultaneous Detention of Multiple Low–Density Lipoprotein Receptor Gene Mutations," *PCR Methods and Applications*, 4(6):352–356 (1995).

Ray et al., "Cosegregation of Codon 807 Mutation of the Canine Rod cGMP Phosphodiesterase β Gene and rcd1," *Inestigative Ophthalmology & Visual Science*, 35(13):4291–4299 (1994).

Ganguly et al., "Conformation–Sensitive Get Electrophoresis for Rapid Detection of Single–Base Differences in Double–Stranded PCR Products and DNA Fragments: Evidence for Solvent–Induced Bends in DNA Heteroduplexes," *PNAS USA*, 90)21):10325–1329 (1993).

Dowton and Slaugh, "Diagnosis of Human Heritable Diseases—Laboratory Approaches and Outcomes," *Clin. Chem.*, 41:785–794 (1995).

Newton et al., "Analysis of Any Point Mutation in DNA. The Amplification Refactory Mutation System (ARMS)," *Nucl. Acids Res.*, 17:2503–2516 (1989).

Haliossos et al., "Modification of Enzymatically Amplified DNA for the Detention of Point Mutations" *Nucl. Acids Res.*, 17:3606 (1989).

Orita et al., "Detention of Polymorphisms of Human DNA by Gel Electrophoresis as Single–Strand Conformation Polymorphisms," *Proc. Natl. Acad. Sci. USA*, 86:2766–2770 (1989).

Sarkar et al., "Screening for Mutations by RNA Single–Strand Conformation Polymorphism (rSSCP): Comparison wit DNA–SSCP," *Nucl. Acids Res.*, 20:871–878 (1992).

Fischer and Lerman, "DNA Fragments Differing by Single Base–Pair Substitutions Are Separated in Denaturing Gradient Gels: Correspondence with Melting Theory," *Proc. Natl. Acad. Sci. USA*, 80:1579–1583 (1983).

Cotton et al., "Reactivity of Cytosine and Thymine in Single–Base–Pair Mismatches with Hydroxylamine and Osmium Tetroxide and its Application to the Study of Mutations," *Proc. Natl. Acad. Sci, USA*, 85:4397–4401 (1988).

Myers et al., *Science*, 230:1242–1246 (1985).

White et al., "Detecting Single Base Substitutions as Heteroduplex Polymorphisms," *Genomics*, 12:301–306 (1992).

* cited by examiner

*Primary Examiner*—Carla J. Myers
(74) *Attorney, Agent, or Firm*—Flehr Hohbach Test Albritton & Herbert LLP

(57) ABSTRACT

Double-stranded conformational polymorphism analysis is performed by combining a probe comprising a cross-linking agent and optionally a label with a sample having a target sequence, which may be complementary or have one or a few mismatches with respect to the probe sequence. After sufficient time for hybridization under mild or lesser stringency conditions, hybridized pairs are irradiated to induce cross-link formation by the cross-linking agent. The sample is then analyzed by denaturing gel electrophoresis where the rate of migration depends upon the degree of complementarity between the probe and the target. For corroboration, in a second experiment, the probe may be combined with the sample under high stringency conditions, where it is found that the formation of cross-linked probe/target is substantially lower for pairs having mismatches than for fully matched pairs. After cross-linking, the sample may be separated by gel electrophoresis, and the amount of cross-linked nucleic acid determined.

23 Claims, No Drawings

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: unknown
      (D) TOPOLOGY: unknown (ii) MOLECULE TYPE: DNA (genomic)

(xi) SEQUENCE DESCRIPTION: SEQ ID NO:1:

CAATACAACA AACCGTTGTG TGATTTGTTA      30

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: unknown
      (D) TOPOLOGY: unknown (ii) MOLECULE TYPE: DNA (genomic)

(xi) SEQUENCE DESCRIPTION: SEQ ID NO:2:

CAATACAACA AACCATTGTG TGATTTGTTA                                      30

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: misc_feature
        (B) LOCATION: 2..3
        (D) OTHER INFORMATION: /note= "Let the 'N' at position 19
            represent an 'X'."

(xi) SEQUENCE DESCRIPTION: SEQ ID NO:3:

ANATCACACA ACGGTTTGTT                                                 20

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:4:

CAATACAACA AACCATTGTG RGATTTGTTA                                      30

(2) INFORMATION FOR SEQ ID NO:5:

(i) SEQUENCE CHARACTERISTICS:
        (A) LENGTH: 56 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:5:

TGACTCCTGA GGAGAAGTCT GCCGTTACTG CCCTGTGGGG CAAGGTGAAC GTGGAT         56

(2) INFORMATION FOR SEQ ID NO:6:

(i) SEQUENCE CHARACTERISTICS:
        (A) LENGTH: 56 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:6:

TGACTCCTGT GGAGAAGTCT GCCGTTACTG CCCTGTGGGG CAAGGTGAAC GTGGAT         56

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

```
    (ix) FEATURE:
          (A) NAME/KEY: misc_feature
          (B) LOCATION: 2..3
          (D) OTHER INFORMATION: /note= "The 'N' at position 2
              represents an 'X'."

(xi) SEQUENCE DESCRIPTION: SEQ ID NO:7:

ANACTTCTCC TCAGGAGT                                                    18

(2) INFORMATION FOR SEQ ID NO:8:

(i) SEQUENCE CHARACTERISTICS:
          (A) LENGTH: 18 base pairs
          (B) TYPE: nucleic acid
          (C) STRANDEDNESS: unknown
          (D) TOPOLOGY: unknown (ii) MOLECULE TYPE: DNA (genomic)

(ix) FEATURE:
          (A) NAME/KEY: misc_feature
          (B) LOCATION: 2..3
          (D) OTHER INFORMATION: /note= "The 'N' at position 2
              represents an 'X'."

(xi) SEQUENCE DESCRIPTION: SEQ ID NO:8:

ANACTTCTCC ACAGGAGT                                                    18
```

DOUBLE-STRANDED CONFORMATIONAL POLYMORPHISM ANALYSIS

CROSS-REFERENCE TO RELATED APPLICATIONS

This application claims priority under 35 U.S.C. §119(e) to U.S. provisional application Ser. No. 60/007,239 filed Nov. 3, 1995.

TECHNICAL FIELD

The field of this invention is detecting mutations in DNA.

BACKGROUND

The amount of genetic information concerning humans and other species has been expanded enormously, particularly with the advent of the human genome project. With identification of all of the genes present, we will be able to identify mutations associated with particular phenotypes. There is already a substantial library of genes, which when mutated, are known to be associated with various diseases. One need only consider cystic fibrosis, Huntington's disease, β-thalassemia, sickle-cell anemia, and the like. In some instances, such as sickle-cell anemia, there is a common point mutation associated with the disease. In other cases, such as cystic fibrosis, there are numerous point mutations spread throughout the genes associated with the disease.

There are many situations where one would wish to know whether a patient or other species has a point mutation or a particular polymorphism of interest. Not only are we interested in diseases, but particularly with other species, there may be an interest in knowing whether the host has a particular allele.

Numerous techniques have been developed to identify differences between a known and target sequence.

Allele-specific oligonucleotide (ASO) tests are used to identify single-nucleotide mismatches or small differences between a short probe and a target DNA. The target DNA is electrophoresed through a gel and subsequently transferred to a nylon or nitrocellulose membrane. A labelled probe is incubated with the membrane under hybridization conditions which distinguish between the presence and absence of complementarity. The test is dependent upon the strict observance of the hybridization and wash conditions necessary to distinguish between mismatches and complementarity.

The polymerase chain reaction (PCR) has been employed to directly detect sequence differences. One technique known as the amplification refractory mutation system (ARMS) is based on the observation that oligonucleotides which are complementary to a given sequence except for a mismatch of the 3' end will not function as a primer for PCR. Thus, by appropriate selection of primer sets and PCR conditions, one can detect a mismatch. Alternatively, primers may be selected that lead to the formation of normal or mutated amplification products, resulting in a restriction site in one or the other sequence.

Single-stranded conformation polymorphism (SSCP) looks to the detection of single-base differences due to differences in migration rates through non-denaturing polyacrylamide gels (PAGE). After denaturing the target DNA, variations in secondary structure of single-strand DNA can be detected using a non-denaturing gel.

Complementary and mismatched DNA—DNA hybrids denature under different conditions from one another. This has been exploited by denaturing gradient gel electrophoresis (DGGE). DGGE gels contain gradually increasing levels of denaturant causing complementary and mismatched dsDNA molecules to migrate and denature at different points in the gel.

In addition to electrophoresis, there are chemical techniques that may be employed, such as chemical modifying agents that cleave the DNA at the mismatched site, e.g. osmium tetroxide, hydroxylamine, etc.; ribonuclease A cleaves DNA:RNA hybrids at mismatch points; which are then followed by analysis with PAGE. Other techniques include heteroduplex analysis and nucleotide sequence analysis. All of these techniques have limitations in the strictness of the conditions and control which must be employed, the complexity of the protocols, limitations on the generality of the methodology, and the like.

Relevant Literature

Articles which describe various techniques for detecting mismatches include: Dowton and Slaugh, *Clin. Chem.* 41:785–794 (1995); Newton et al., *Nucl. Acids Res.* 17:2503–2516 (1989); Haliassos et al., *Nucl. Acids Res.* 17:3606 (1989); Orita et al., *Proc. Natl. Acad. Sci. USA* 86:2766–2770 (1989); Sarkar et al., *Nucl. Acids. Res.* 20:871–878 (1992); Fischer and Lerman, *Proc. Natl. Acad. Sci. USA* 80:1579–1583 (1983); Cotton et al., *Proc. Natl. Acad. Sci. USA* 85:4397–4401 (1988); Myers et al., *Science* 230:1242–1246 (1985); and White et al., *Genomics* 12:301–306 (1992).

SUMMARY OF THE INVENTION

Methods and compositions are provided for detection of single or multiple mismatches between a target sequence and a known sequence. The method comprises hybridizing under not greater than mild stringency conditions a probe and a target sequence of less than about 300 bases. The probe comprises the known sequence, optionally a detectable label, and a cross-linking agent. After sufficient time for hybridization to occur for a detectable amount of double-stranded nucleic acid, the conditions of the medium are changed to induce cross-linking of hybridized pairs. The sample is then separated using PAGE under denaturing conditions and the migratory rate of the labelled probe cross-linked to target nucleic acid determined as against a known standard. A probe/target pair with mismatches will migrate at a different rate from a complementary probe/target pair. For confirmation, more stringent hybridization conditions can be selected where the amount of hybridization between a mismatched pair of sequences and a matched pair of sequences is substantially different. The resulting sample is heated the same way as indicated above, where the amount of probe which becomes cross-linked is related to the degree of mismatches between the probe and target, there being a substantially smaller amount of cross-linked probe in the case of a mismatch. In accordance with the subject invention, substantially increased flexibility is obtained as to the conditions which may be employed for determining the presence of a mutation in a target sequence.

DESCRIPTION OF THE SPECIFIC EMBODIMENTS

In accordance with the subject invention, probes are provided to be used in methods for detecting the presence or absence of mismatches to the probe in a target sequence. The mismatches may be as a result of a mutation, allelic variation, species variation, alternative splicing, etc. The mismatch may be an insertion, deletion or mismatched pairing, usually one or more point mismatches.

Generally, the method employs combining the probe, which is characterized by having a known sequence, optionally a detectable label and a cross-linking agent, with a target sequence, which may be present as a major component of the DNA from the target or as one member of a complex mixture. The target sequence is provided in single-stranded form. The probe and target sequence are allowed to hybridize under not greater than mild stringency conditions. After sufficient time for a sufficient amount of double-stranded nucleic acid to form, the conditions are changed so as to provide for cross-linking. After cross-linking has occurred, the sample is then separated by gel electrophoresis, where the migratory rate of a mismatched double-stranded nucleic acid is different from the migratory rate of a complementary double-stranded nucleic acid. The observed migratory rate of the probe-target double-stranded complex may be compared with a standard to determine the presence or absence of mismatches.

The target DNA may come from any source and will be provided as an average size in the range of about 25 to 300 nt, more usually 50–250 nt, preferably from about 50–200 nt. The source of DNA may be prokaryotic or eukaryotic, usually eukaryotic. The source may be the genome of the host, plasmid DNA, viral DNA, where the virus may be naturally occurring or serving as a vector for DNA from a different source, a PCR amplification product, or the like. The target DNA may be a particular allele of a mammalian host, an MHC allele, a sequence coding for an enzyme isoform, a particular gene or strain of a unicellular organism, or the like. The target sequence may be genomic DNA, cDNA, RNA, or the like.

Nucleic acids of the desired length can be achieved, particularly with DNA, by restriction, use of PCR and primers, and the like. Desirably, at least about 80 mol %, usually at least about 90 mol % of the target sequence, will have the same size. For restriction, a frequently cutting enzyme may be employed, usually an enzyme with a four base consensus sequence, or combination of restriction enzymes may be employed, where the DNA will be subject to complete digestion. The mismatch will normally be internal to the target fragment and will normally not be at a site cleaved by a restriction enzyme used to digest the sample DNA. Typical sequences of interest include the mutation in sickle-cell anemia, the MHC associated with IDDM, mutations associated with cystic fibrosis, Huntington's disease, β-thalassemia, Alzheimer's disease, and various cancers, such as those caused by activation of oncogenes (e.g. ras, src, myc, etc.) and/or inactivation of tumor suppressants (e.g. p53, RB, etc.). In some cases, such as sickle-cell anemia, there is a single mutation. In other cases, such as cystic fibrosis, there are multiple mutations to be determined. By selection of appropriate restriction enzymes, one can provide that the region suspected of harboring one or more mutations is present on a fragment of predetermined size, so that by using a combination of probes, one can readily detect the presence of one or more of the mutations in the gene.

Depending upon the source of DNA, the DNA may be subject to some purification, such as separation of proteins, removal of restriction enzyme inhibitors, or the like.

The probe will generally be of about 15 to 50 nt, more usually of from about 20 to 35 nt. The probe may have from 1 to 5 cross-linking agents, more usually from about 1 to 3 cross-linking agents. The cross-linking agents will be selected so as not to interfere with the hybridization and will generally be positioned across from a thymidine (T), cytidine (C), or uridine (U) to provide for cross-linking. A large number of functionalities are photochemically active and can form a covalent bond with almost any organic moiety. These groups include carbenes, nitrenes, ketenes, free radicals, etc. One can provide for a scavenging molecule in the bulk solution, normally excess non-target nucleic acid, so that probes which are not bound to a target sequence will react with the scavenging molecules to avoid non-specific cross-linking between probes and target sequences. Carbenes can be obtained from diazo compounds, such as diazonium salts, sulfonylhydrazone salts, or diaziranes. Ketenes are available from diazoketones or quinone diazides. Nitrenes are available from aryl azides, acyl azides, and azido compounds. For further information concerning photolytic generation of an unshared pair of electrons, see A. Schonberg, Preparative Organic Photochemistry, Springer-Verlag, NY 1968.

For the most part, the compounds which are employed for cross-linking will be photoactivatable compounds which form covalent bonds with a base, particularly a pyrimidine. These compounds will include functional moieties, such as coumarin, as present in substituted coumarins, furocoumarin, isocoumarin, bis-coumarin, psoralen, etc., quinones, pyrones, α,β-unsaturated acids, acid derivatives, e.g. esters, ketones, and nitriles; azido, etc.

Another class of photoactive reactants are organometallic compounds based on any of the d- or f-block transition metals. Photoexcitation induces the loss of a ligand from the metal to provide a vacant site available for substitutions. Suitable ligands include nucleotides. For further information regarding the photosubstitution of organometallic compounds, see "Organometallic Photochemistry", G. F. Geoffrey and M. S. Wrighton, Academic Press, San Francisco, Calif., 1979.

The probe homologous sequence which binds to the target sequence will usually contain naturally occurring nucleotides. However, in some instances the phosphate-sugar chain may be modified by using unnatural sugars, by substituting oxygens of the phosphate with sulfur, carbon, nitrogen, or the like, or other modification which can provide for synthetic advantages, stability under the conditions of the assay, resistance to enzymatic degradation, etc.

The probes may be prepared by any convenient method, most conveniently synthetic procedures, where the cross-linking modified nucleotide is introduced at the appropriate position stepwise during the synthesis. Linking of various molecules to nucleotides is well known in the literature and does not require description here. See, for example, "Oligonucleotides and Analogues. A Practical Approach", Eckstein, F. ed., Oxford University Press, 1991.

Similarly, the label, if present, may be bonded to any convenient nucleotide in the probe chain, where it does not interfere with the hybridization between the probe and the target sequence. Labels will generally be small, usually from about 100 to 1,000 Da. The labels may be any detectable entity, where the label may be able to be detected directly, or by binding to a receptor, which in turn is labelled with a molecule which is readily detectable. Molecules which provide for detection in electrophoresis include radiolabels, e.g. $^{32}P$, $^{35}S$, etc. fluorescers, such as rhodamine, fluorescein, etc. ligand for receptors, such as biotin for streptavidin, digoxigenin for anti-digoxigenin, etc., chemiluminescers, and the like. Alternatively, no label need be used, where the DNA may be stained either prior to, during or after the separation, using such stains as ethidium bromide, ethidium dimer, thiazole orange, thiazole blue, dimers thereof, or the like. When using PCR, one can provide for the primer to be labelled, rather than the probe, so that the primer may provide for the detection. Where a ligand is employed, the receptor may be labelled with any of the directly detectable labels.

The method is performed by combining the probe with the target DNA. Usually, the target DNA will be estimated to be present in the range of about $10^{-20}$ to $10^{-8}$ moles, more usually in the range of about $10^{-17}$ to $10^{-10}$ moles. The probe may be present in equivalent amount or large excess, generally in excess not more than $10^9$-fold, more usually in excess not more than $10^7$- fold, based on the estimated amount of target nucleic acid. The hybridizing medium will provide for mild to low stringency, to ensure that substantially all of the target nucleic acid is cross-linked. Generally, the stringency will be equivalent to a temperature in the range of about 25–70° C., frequently 40–70° C., more usually 30–50° C., with 0.05–1.5 M sodium, more usually 0.25–1 M sodium ion or 0–20% formamide. With RNA, guanidinium thiocyanate may be added in an amount of 0.1 to 6M. Other denaturants besides formamide include urea and dimethylsulfoxide. The hybridization conditions are selected to afford the maximum amount of hybridization between the probe and target-sequence for both the matched and mismatched nucleic acid sequences. The time for the hybridization will be sufficient to form a detectable amount of double-stranded nucleic acid, will be dependent upon the conditions of the hybridization, and the sensitivity with which the label can be detected. Times will usually be at least 5 minutes and not more than 6 hours, more usually about 10 minutes–1 hour.

After the hybridization has occurred, the probe-containing double-stranded nucleic acid may be cross-linked. The light will be at or greater than 300 nm to avoid naturally occurring cross-linking of nucleic acid. Generally, the light will be in the range of 300–400 nm using a light source in conjunction with a Pyrex filter. While chemical activation may be employed, normally photolytic activation is more convenient and will be the method of choice. The irradiation time will generally be in the range of about 1 minute to 2 hours, more usually in the range of about 5 minutes to 1 hour, depending upon the size of the sample, the power of the irradiating source, the desired amount of product, and the like. If desired, an aliquot of the sample will be taken and electrophoresed to determine whether a sufficient amount of cross-linking has occurred.

After the irradiation, the sample may then be treated, such as by heating, or combined with a front-running dye, glycerol, sucrose, formamide, etc. for loading purposes. These techniques are well known in the art and do not require elaboration here.

The electrophoresis is carried out using polyacrylamide gel, generally 5–23% acrylamide and a ratio of 10–30:1 of acrylamide to bis-monomer. Denaturing conditions are used so as to remove any non-cross-linked nucleic acid from the region of the cross-linked nucleic acid. Other denaturants may be used in place of urea. Any of the typical running buffers may be employed such as Tris-borate-EDTA. The electrophoresis is carried out under conventional conditions to allow for separation between mismatched and matched sequences. Having an appropriately matched or mismatched standard in one of the lanes, one can compare the band in the sample lane with the standard band. The differences between the standard and the sample will indicate whether the target sequence is different from the standard sequence. By using the appropriate label, or staining the gel, one can detect the presence or absence of any mismatches between the target and probe sequences.

If one wishes further corroboration, one can use an adaptation of the ASO technique, determining the degree of duplex formation. However, providing for cross-linking substantially diminishes the criticality of the conditions employed. In this procedure, the temperature will generally be in the range of about 50–70° C., while the sodium ion concentration will generally be in the range of about 50–500 mM, more usually about 100–400 mM. For each target sequence and probe, one would optimize the conditions so as to obtain the greatest difference in the degree of duplex formation between mismatched sequences and matched sequences. Desirably, there should be at least about 2, usually at least about a 5-fold ratio, between the amount of cross-linked matched sequences and cross-linked, non-matched sequences. In this process, higher stringency conditions are employed. Otherwise, the conditions will be substantially the same as the conditions employed for the differences in migration. The amount of cross-linked DNA can be readily determined by measuring the signal obtained from the band associated with the matched standard and the probe and target sequence. Where the signal is substantially less, this would indicate that the sequences are mismatched. Where the signal is about the same as the standard, this would indicate that the sequences are matched.

For convenience of the user, kits may be provided comprising one or more, usually 2 or more probes, particularly a pair of probes, where one probe is complementary to a sequence, which may be referred to as the "wild-type" sequence, and the other probe may be referred to as the "mutant" sequence. However, it should be understood that these designations are arbitrary, since in many situations one may only wish to know whether the target sequence is the same or different from the probe sequence, without there being the concept that one sequence is common or wild-type and the other sequence is uncommon or mutant. For example, one may wish to know which of two MHC alleles are present which differ by one or two mismatches. The pair of probes will usually have not more than 5, more usually not more than 3 differences. Depending upon the target sequence, there may be a plurality of probes, particularly pairs of probes, usually not more than about 12 pairs, where the target sequence has a plurality of potential mutations, which may be spread through the gene. Ancillary materials may be provided, such as dyes, labeled antibodies, where a ligand is used as a label, labeled primers for use with PCR, etc.

The following examples are offered by way of illustration and not by way of limitation.

EXPERIMENTAL

Example 1

Detection of a single-base mismatch by (A) allele-specific hybridization and cross-linking and (B) DSCP analysis An oligonucleotide (oligo #1) comprising nucleotides 374–403 of the E6 gene of human papilloma virus type 16 was synthesized by the phosphoramidite method of DNA synthesis and labeled with $^{32}$P at the 5' end, A second $^{32}$P-labeled oligonucleotide (oligo #2) containing the same sequence as oligo #1 except for a single G→A base change at position 388 was also prepared.

Oligo #1: 5'-CAA TAC AAC AAA CCG TTG TGT GAT TTG TTA-3' (SEQ ID NO: 1)

Oligo #2: 5'-CAA TAC AAC AAA CCA TTG TGT GAT TTG TTA-3' (SEQ ID NO: 2)

A 20-mer DNA probe (oligo #3) containing the photoactive cross-linking group, 3-O-(7-coumarinyl) glycerol (denoted by X in the sequence) was prepared. This DNA sequence of this probe is fully complementary to oligo #1 but would hybridize with oligo #2 to form a duplex containing an A/C mismatch.

Oligo #3: 3'-TTG TTT GGC AAC ACA CTA XA-5' (SEQ ID NO: 3)

Oligo #1/#3 duplex:

5'-CAA TAC AAC AAA CCG TTG TGT GAT TTG TTA-3' (SEQ ID NO: 1) 3'-TTG TTT GGC AAC ACA CTA XA-5' (SEQ ID NO: 3)

Oligo #2/#3 duplex:

5'-CAA TAC AAC AAA CCA TTG TGR GAT TTG TTA-3' (SEQ ID NO: 4) 3'-TTG TTT GGC AAC ACA CTA XA-5' (SEQ ID NO: 3)

Oligo #3 (20 pmole) was incubated in the presence of 2 pmole of either $^{32}$P-5' end-labeled oligo #1 or oligo #2 in 0.15 mL samples at the temperatures and NaCl concentrations summarized below:

| Sample | Oligonucleotides | Temp., ° C. | NaCl conc., mM |
|---|---|---|---|
| 1 | 1 + 3 | 45 | 150 |
| 3 | 1 + 3 | 45 | 300 |
| 2 | 2 + 3 | 45 | 150 |
| 4 | 2 + 3 | 45 | 300 |
| 5 | 1 + 3 | 50 | 150 |
| 7 | 1 + 3 | 50 | 300 |
| 6 | 2 + 3 | 50 | 150 |
| 8 | 2 + 3 | 50 | 300 |
| 9 | 1 + 3 | 55 | 150 |
| 11 | 1 + 3 | 55 | 300 |
| 10 | 2 + 3 | 55 | 150 |
| 12 | 2 + 3 | 55 | 300 |

After 20 minutes incubation, the solutions were irradiated under UV-A wavelength light for 45 minutes. Upon completion of the irradiation step, one-tenth of the samples (0.015 mL) was removed and mixed with an equal volume of formamide-bromophenol blue dye mix and heated to 70° C. for 3 minutes. The samples were cooled on ice and loaded onto a 15% polyacrylamide gel (19:1 acrylamide/bisacrylamide) containing 7 M urea and electrophoresed at 300 V until the bromophenol blue dye reached the bottom of the gel. The gel was taken down and exposed to X-ray film overnight at −80° C.

Method 1: Allele specific hybridization and cross-linking

By carrying out the experiment under a range of hybridization temperatures (45–55° C.) and NaCl concentration (150–300 mM), it was possible to define condition that led to appreciable cross-link formation between the complementary oligonucleotides #1 and #3 but not the mismatched oligonucleotides #2 and #3. To determine the best conditions for mismatch discrimination the radioactive bands were excised from the gel, quantified by scintillation counting and the percent yield of cross-linked product measured (relative to unreacted $^{32}$P-labeled oligonucleotide). The results are shown below:

| Sample | Oligonucleotides | Temp., ° C. | NaCl conc., mM | cross-linking, % |
|---|---|---|---|---|
| 1 | 1 + 3 | 45 | 150 | 46 |
| 2 | 2 + 3 | 45 | 150 | 44 |
| 3 | 1 + 3 | 45 | 300 | 49 |
| 4 | 2 + 3 | 45 | 300 | 51 |
| 5 | 1 + 3 | 50 | 150 | 40 |

-continued

| Sample | Oligonucleotides | Temp., ° C. | NaCl conc., mM | cross-linking, % |
|---|---|---|---|---|
| 6 | 2 + 3 | 50 | 150 | 22 |
| 7 | 1 + 3 | 50 | 300 | 48 |
| 8 | 2 + 3 | 50 | 300 | 44 |
| 9 | 1 + 3 | 55 | 150 | 39 |
| 10 | 2 + 3 | 55 | 150 | 3 |
| 11 | 1 + 3 | 55 | 300 | 43 |
| 12 | 2 + 3 | 55 | 300 | 18 |

From the data in the above table, it can be determined that the optimal conditions for discriminating the complementary and mismatched duplexes are those used in samples 9 and 10 (55° C., 150 mM NaCl); under these conditions the complementary oligonucleotide pair yields 13-fold more cross-linked product than the mismatched pair (39% vs. 3%).

Method 2: DSCP analysis (Double-stranded conformational polymorphism analysis)

Analysis of the autoradiogram for the samples (3 and 4) run under the least stringent hybridization conditions (45° C., 300 mM NaCl) clearly showed that the product obtained from cross-linking between the mismatched oligonucleotides #2 and #3 migrated slower through the gel than the product obtained from cross-linking the complementary oligonucleotides #1 and #3 (the DSCP effect).

The results obtained from this experiment highlighted two advantages of the DSCP method over the more conventional method of developing hybridization conditions to detect single base mismatches:

1. The DSCP method is simple and does not require the careful optimization of hybridization conditions to distinguish matched from mismatched sequences. The DSCP method uses non-stringent hybridization conditions.

2. By using non-stringent conditions the cross-link yield and hence the signal in the assay is higher than when the hybridization stringency method is employed; under the conditions used for DSCP analysis (45° C., 300 mM NaCl) the cross-link yield for the reaction between the complementary oligonucleotides #1 and #3 was 49%, however under the conditions that led to the best mismatch discrimination with the hybridization stringency method (55° C., 150 mM NaCl), the cross-linking efficiency was 39%. Thus the DSCP method resulted in 26% greater signal.

Example 2

Detection of normal ($\beta^A$) and sickle cell ($\beta^S$) β-globin alleles by DSCP analysis Two 56 base oligonucleotides comprising a portion of the sequence of either the normal human β-globin gene ($\beta^A$-target) or the sickle cell β-globin gene ($\beta^S$-target) were synthesized by the phosphoramidite method of DNA synthesis and labeled with $^{32}$P at their 5' ends. The $\beta^S$-globin target sequence differs from the $\beta^A$-target by a single A→T mutation that gives raise to a mutant β-globin protein that contains valine instead of glutamic acid.

$\beta^A$-target: 5'-TGA CTC CTG AGG AGA AGT CTG CCG TTA CTG CCC TGT-GGG GCA AGG TGA ACG TGG AT-3' (SEQ ID NO: 5)

$\beta^S$-target: 5'-TGA CTC CTG TGG AGA AGT CTG CCG TTA CTG CCC TGT-GGG GCA AGG TGA ACG TGG AT-3' (SEQ ID NO: 6)

Two probes complementary to either the $\beta^A$-target sequence $\beta^A$-probe) or the $\beta^S$-target ($\beta^S$-probe) were also synthesized. These probes were modified with the photoactive cross-linking group, 3-O-(7-coumarinyl) glycerol (denoted by X in the sequence):

$\beta^A$-probe: 3'-TGA GGA CTC CTC TTC AXA-5' (SEQ ID NO: 7)
$\beta^S$-probe: 3'-TGA GGA CAC CTC TTC AXA-5' (SEQ ID NO: 8)

Hybridization and cross-linking experiments were carried out to show that DSCP with the two β-globin probes could be used to detect and distinguish the presence of either the β-globin targets when the target molecules were present individually or together in a 1:1 mixture (as would be found in a heterozygous individual). The experiments summarized below were carried out:

| Sample | β-Globin probe | β-Globin target | UV-A irradiation |
|---|---|---|---|
| 1 | $\beta^A$ | $\beta^A$ | − |
| 2 | $\beta^S$ | $\beta^S$ | − |
| 3 | $\beta^A$ | $\beta^A$ | + |
| 4 | $4\beta^A$ | $\beta^S$ | + |
| 5 | $\beta^S$ | $\beta^S$ | + |
| 6 | $\beta^S$ | $\beta^A$ | + |
| 7 | $\beta^A$ | $\beta^A/\beta^S$ | + |
| 8 | $\beta^S$ | $\beta^A/\beta^S$ | + |

Each 0.05 mL sample contained 10 pmole of the relevant probe and 0.2 pmole of $^{32}$P-labeled target (samples 7 and 8 contained 0.2 pmole of each target molecule). The NaCl concentration of the solutions was 0.75 M.

Hybridization was carried out at 35° C. for 20 minutes at which time the samples were irradiated with a UV-A light source for 60 minutes. One-fifth of the samples (0.010 mL) was removed and mixed with an equal volume of formamide-bromophenol blue dye mix and heated to 70° C. for 3 minutes. The samples were cooled on ice and loaded onto a 10% polyacrylamide gel (19:1 acrylamide/bisacrylamide) containing 7 M urea and electrophoresed at 300 V until the bromophenol blue dye reached the bottom of the gel. The gel was taken down and exposed to X-ray film overnight at −80° C.

The data obtained in the experiment showed that by using either of the two cross-linker-modified probes, it was possible to employ DSCP analysis to detect and distinguish the two β-globin alleles. The major cross-linked products obtained from reaction between the fully complementary $\beta^A$-probe and $\beta^A$-target (sample 3) and the $\beta^S$-probe and $\beta^S$-target (sample 5) migrated through the gel significantly faster than the products obtained after cross-linking between the mismatched probes and targets (samples 4 and 6). Furthermore, analysis of the reactions carried out in the presence of both the $\beta^A$- and $\beta^S$-targets (samples 7 and 8), showed that the two probes were able to detect and distinguish both alleles simultaneously. This finding is clinically relevant since individuals who are carriers of sickle-cell anemia possess both the $\beta^A$- and $\beta^S$-alleles in their DNA.

It is evident from the above results, that a simple, and accurate technique is provided which can readily detect single base mismatches. The methodology is convenient, the assay can be rapidly carried out, and is not subject to error due to minor changes in control of the conditions.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of detecting the presence or absence of at least one mismatch between a nucleic acid probe and a nucleic acid target, wherein said probe and target have sequences which differ by not more than five nucleotide base pair mismatches and wherein said probe comprises a known polynucleotide sequence and a sugar and base free photoactivatable cross-linking coumarinyl glycerol group occupying a nucleotide position between two nucleotides of said known polynucleotide sequence, which when said probe sequence is hybridized to said target sequence, upon photoactivation forms a covalent bond between said probe sequence and said target sequence, said method comprising:

combining, in a hybridizing medium, a nucleic acid sample comprising said target and said probe under mild stringency hybridizing conditions for a time sufficient for said target and said probe to hybridize;

irradiating said hybridizing medium to form cross-links between said probe and target sequence to which said probe is hybridized to from cross-linked double-stranded nucleic acid;

separating nucleic acid in said hybridizing medium by denaturing electrophoresis and comparing the migratory rate of said cross-linked double-stranded nucleic acid to a known mismatched or matched cross-linked double-stranded nucleic acid standard, whereby the presence or absence of said at least one mismatch is determined.

2. A method according to claim 1, wherein said probe is labeled with a detectable label.

3. A method according to claim 1, wherein said sample is prepared using the polymerase chain reaction and said sample nucleic acid is labeled with a detectable label.

4. A method according to claim 1, wherein said electrophoresis is polyacrylamide gel electrophoresis.

5. A method of detecting the presence or absence of at least one mismatch between a nucleic acid probe and a nucleic acid target, wherein said probe and target have sequences which differ by not more than five nucleotide base pair mismatches and wherein said target sequence comprises a nucleic acid molecule of from about 25 to 300 nt and said probe comprising a known polynucleotide sequence of from 15 to 50 nt and a sugar and base free photoactivatable cross-linking coumarinyl glycerol group occupying a nucleotide position between two nucleotides of said known polynucleotide sequence, which when said probe sequence is hybridized to said target sequence, upon photoactivation forms a covalent bond between said probe sequence and said target sequence, said method comprising:

combining, in a hybridizing medium, a nucleic acid sample comprising said target and said probe under mild stringency hybridizing conditions for a time sufficient for said target and said probe to hybridize;

irradiating at a wavelength in the range of about 300–400 nm said hybridizing medium to form cross-links between said probe and target sequence to which said probe is hybridized to cross-linked double-stranded nucleic acid;

separating nucleic acid in said hybridizing medium by denaturing electrophoresis and comparing the migratory rate of said cross-linked double-stranded nucleic acid to a known mismatched or matched cross-linked double-stranded nucleic acid standard, whereby the presence or absence of said at least one mismatch is determined.

6. A method according to claim 5, wherein said sample is prepared by restriction enzyme digestion of genomic DNA.

7. A method according to claim 5, wherein said sample is prepared using the polymerase chain reaction and said sample nucleic acid is labeled with a detectable label.

8. A method according to claim 5, wherein said probe is labeled with a detectable label.

9. A method according to claim 5, wherein said electrophoresis is polyacrylamide gel electrophoresis.

10. A method of detecting the presence or absence of at least one mismatch between a nucleic acid probe and a nucleic acid target, wherein said probe and target have sequences which differ by not more than five nucleotide base pair mismatches, said target sequence comprising a nucleic acid molecule of from about 25 to 300 nt and wherein said probe comprises a known polynucleotide sequence of from 15 to 50 nt and a sugar and base free photoactivatable cross-linking coumarinyl glycerol group occupying a nucleotide position between two nucleotides of said known polynucleotide sequence, which when said probe sequence is hybridized to said target sequence, upon photoactivation forms a covalent bond between said probe sequence and said target sequence, said method comprising:

combining, in a hybridizing medium, a nucleic acid sample comprising said target and said probe under mild stringency hybridizing conditions equivalent to a temperature in the range of 25–70° C. and with 0.1–1.5 M sodium for a time sufficient for said target and said probe to hybridize;

irradiating at a wavelength in the range of about 300–400 nm said hybridizing medium to form cross-links between said probe and target sequence to which said probe is hybridized to from cross-linked double-stranded nucleic acid;

separating nucleic acid in said hybridizing medium by denaturing gel electrophoresis and comparing the migratory rate of said cross-linked double-stranded nucleic acid to a known mismatched or matched cross-linked double-stranded nucleic acid standard, whereby the presence or absence of said at least one mismatch is determined.

11. A method of detecting the presence or absence of at least one mismatch between a nucleic acid probe and a nucleic acid target, wherein said probe and target have sequences which differ by not more than five nucleotide base pair mismatches, said target sequence comprising a nucleic acid molecule of from about 25 to 300 nt and said probe comprising a known polynucleotide sequence of from 15 to 50 nt and a sugar and base free photoactivatable cross-linking coumarinyl (glycerol group occupying a nucleotide position between two nucleotides of said known polynucleotide sequence, which when said probe sequence is hybridized to said target sequence, upon photoactivation forms a covalent bond between said probe sequence and said target sequence, said method comprising:

combining, in a hybridizing medium, a nucleic acid sample comprising said target and said probe under high stringency hybridizing conditions for a time sufficient for said target and said probe to hybridize, where a probe complementary to said target results in at least about a 2-fold greater amount of hybridization than a mismatched probe;

irradiating at a wavelength in the range of about 300–400 nm said hybridizing medium to form cross-links between said probe and target sequence to which said probe is hybridized to cross-linked double-stranded nucleic acid;

separating nucleic acid in said hybridizing medium by denaturing electrophoresis and determining the amount of cross-linked double-stranded nucleic acid, where the amount of cross-linked double-stranded nucleic acid is related to the presence or absence of mismatches between said probe and said target.

12. A method according to claim 11, wherein said high stringency conditions are at least equivalent to a temperature in the range of about 40–70° C. and 0.05 to 0.5 M sodium ion.

13. A kit comprising two probes, characterized by consisting of 15 to 20 nt, joined to each of said probes is a sugar and base free photoactivatable cross-linking coumarinyl gylcerol group occupying a nucleotide position between two nucleotides of each of said probes, each of said probes differing with the other probe by not more 3 mismatches, and being naturally occurring sequences.

14. A kit according to claim 13, wherein said naturally occurring sequences are related by one being the mutant of the other.

15. A kit according to claim 13, wherein said naturally occurring sequences are related by one being the allele of the other.

16. A kit according to claim 13, wherein said probes are labeled with a detectable label.

17. A kit according to claim 13, wherein each of said probes has a plurality of cross-linking coumarinyl glycerol groups.

18. A method according to claim 1 wherein said photoactivatable cross-linking coumarinyl glycerol group is 3-O-(7-coumarinyl) glycerol.

19. A kit according to claim 13 wherein said photoactivatable cross-linking coumarinyl glycerol group is 3-O-(7-coumarinyl) glycerol.

20. A method of detecting the presence or absence of at least one mismatch between a nucleic acid probe and a nucleic acid target, wherein said probe and target have sequences which differ by not more than five nucleotide base pair mismatches and wherein said probe comprises a known polynucleotide sequence and a coumarinyl glycerol photoactivatable cross-linking agent occupying a nucleotide position between two nucleotides of said known polynucleotide sequence, which when said probe sequence is hybridized to said target sequence, upon photoactivation forms a covalent bond between said probe sequence and said target sequence, said method comprising:

combining, in a hybridizing medium, a nucleic acid sample comprising said target and said probe under mild stringency hybridizing conditions for a time sufficient for said target and said probe to hybridize;

irradiating said hybridizing medium to form cross-links between said probe and target sequence to which said probe is hybridized to from cross-linked double-stranded nucleic acid;

separating nucleic acid in said hybridizing medium by denaturing electrophoresis and comparing the migratory rate of said cross-linked double-stranded nucleic acid to a known mismatched or matched cross-linked double-stranded nucleic acid standard, whereby the presence or absence of said at least one mismatch is determined.

21. A method of detecting the presence or absence of at least one mismatch between a nucleic acid probe and a nucleic acid target, wherein said probe and target have sequences which differ by not more than five nucleotide base pair mismatches and wherein said probe comprises a known polynucleotide sequence and photoactivatable cross-linking coumarinyl glycerol group occupying a nucleotide position between two nucleotides of said known polynucleotide sequence and said coumarinyl glycerol group is not appended to a sugar or base of said known polynucleotide sequence, which when said probe sequence is hybridized to said target sequence, upon photoactivation forms a covalent bond between said probe sequence and said target sequence, said method comprising:

combining, in a hybridizing medium, a nucleic acid sample comprising said target and said probe under mild stringency hybridizing conditions for a time sufficient for said target and said probe to hybridize;

irradiating said hybridizing medium to form cross-links between said probe and target sequence to which said probe is hybridized to from cross-linked double-stranded nucleic acid;

separating nucleic acid in said hybridizing medium by denaturing electrophoresis and comparing the migratory rate of said cross-linked double-stranded nucleic acid to a known mismatched or matched cross-linked double-stranded nucleic acid standard, whereby the presence or absence of said at least one mismatch is determined.

22. A method of detecting the presence or absence of at least one mismatch between a nucleic acid probe and a nucleic acid target, wherein said probe and target have sequences which differ by not more than five nucleotide base pair mismatches and wherein said probe comprises a known polynucleotide sequence and 3-O-(7-coumarinyl) glycerol occupying a nucleotide position between two nucleotides of said known polynucleotide sequence, which when said probe sequence is hybridized to said target sequence, upon photoactivation forms a covalent bond between said probe sequence and said target sequence, said method comprising:

combining, in a hybridizing medium, a nucleic acid sample comprising said target and said probe under mild stringency hybridizing conditions for a time sufficient for said target and said probe to hybridize;

irradiating said hybridizing medium to form cross-links between said probe and target sequence to which said probe is hybridized to from cross-linked double-stranded nucleic acid;

separating nucleic acid in said hybridizing medium by denaturing electrophoresis and comparing the migratory rate of said cross-linked double-stranded nucleic acid to a known mismatched or matched cross-linked double-stranded nucleic acid standard, whereby the presence or absence of said at least one mismatch is determined.

23. A kit comprising two probes, characterized by consisting of 15 to 20 nt, joined to each of said probes is 3-O-(7-coumarinyl) glycerol occupying a nucleotide position between two nucleotides of each of said probes, each of said probes differing with the other probe by not more 3 mismatches, and being naturally occurring sequences.

* * * * *

UNITED STATES PATENT AND TRADEMARK OFFICE
CERTIFICATE OF CORRECTION

PATENT NO. : 6,187,532 B1  Page 1 of 1
DATED : February 13, 2001
INVENTOR(S) : Michael Wood et al.

It is certified that error appears in the above-identified patent and that said Letters Patent is hereby corrected as shown below:

Column 6,
Line 9, delete "30".
Line 55, change "(oligo #1)" to -- (oligonucleotide #1) --.
Line 59, change "(oligo #2)" to -- (oligonucleotide #2) --.

Column 7,
Line 12, change "TGR" to -- TGT --.

Column 8,
Lines 61 and 64, change "TGT-GGG" to -- TGT GGG --.

Column 9,
Line 7, after "DSCP", insert -- analysis --.
Line 19, in Sample 4, change "$4\beta^A$" to -- $\beta^A$ --.

Column 15,
Line 39, change "(glycerol" to -- glycerol --.

In all the (A)LENGTH, change the units from "base pairs" to -- base --.

Column 11,
Line 16, change "at position 19" to -- at position 2 --.
Line 30, change "RGATTTGTTA" to -- TGATTTGTTA --.

Signed and Sealed this

Fifteenth Day of October, 2002

Attest:

Attesting Officer

JAMES E. ROGAN
Director of the United States Patent and Trademark Office